(12) United States Patent
Hodson et al.

(10) Patent No.: US 8,616,196 B2
(45) Date of Patent: Dec. 31, 2013

(54) INHALATION DEVICE AND A METHOD FOR ASSEMBLING SAID INHALATION DEVICE

(75) Inventors: Darren Hodson, Leicestershire (GB); William Treneman, Cambridgeshire (GB)

(73) Assignee: AstraZeneca AB, Sodertaije (SE)

(*) Notice: Subject to any disclaimer, the term of this patent is extended or adjusted under 35 U.S.C. 154(b) by 1384 days.

(21) Appl. No.: 11/571,389

(22) PCT Filed: Jun. 23, 2005

(86) PCT No.: PCT/SE2005/000994
§ 371 (c)(1),
(2), (4) Date: Dec. 28, 2006

(87) PCT Pub. No.: WO2006/004496
PCT Pub. Date: Jan. 12, 2006

(65) Prior Publication Data
US 2008/0083408 A1    Apr. 10, 2008

(30) Foreign Application Priority Data
Jul. 2, 2004    (SE) ...................................... 0401773

(51) Int. Cl.
*A61M 11/00*    (2006.01)

(52) U.S. Cl.
USPC ................................ 128/200.23; 128/205.23

(58) Field of Classification Search
USPC ............. 128/200.14, 200.19, 202.22, 203.23, 128/200.23, 205.23; 222/41, 38, 43, 45, 47, 222/49
See application file for complete search history.

(56) References Cited

U.S. PATENT DOCUMENTS

| | | |
|---|---|---|
| 4,817,822 A | 4/1989 | Rand et al. |
| 5,411,173 A | 5/1995 | Weinstein |
| 5,482,030 A | 1/1996 | Klein |
| 5,505,192 A * | 4/1996 | Samiotes et al. ......... 128/200.14 |
| 5,718,355 A | 2/1998 | Garby et al. |
| 5,724,957 A | 3/1998 | Rubsamen et al. |
| 6,082,358 A | 7/2000 | Scarrott et al. |
| 6,435,372 B1 | 8/2002 | Blacker et al. |
| 6,446,627 B1 | 9/2002 | Bowman et al. |
| 6,971,381 B2 * | 12/2005 | Langford ................. 128/200.23 |
| 7,308,893 B2 * | 12/2007 | Boot ....................... 128/203.15 |
| 7,464,708 B2 * | 12/2008 | Marx ....................... 128/205.23 |

(Continued)

FOREIGN PATENT DOCUMENTS

| | | |
|---|---|---|
| EP | 0381494 | 8/1990 |
| EP | 0684047 | 11/1995 |

(Continued)

*Primary Examiner* — Steven Douglas
(74) *Attorney, Agent, or Firm* — Finnegan, Henderson, Farabow, Garrett & Dunner, LLP

(57) ABSTRACT

An inhalation device for delivering doses of medicament to a user comprising: —a canister (5), said canister being adapted to accommodate the medicament to be dispensed to a user, and —a counter (15) which is connected to the canister (5). According to the invention —the canister (5) is adapted to receive the counter (15) on a base end (6a), —the counter and/or the canister further having contact parts (18, 20) for their attachment having means for increasing the friction and thereby allowing the counter to fixedly be attached onto the canister in a range of different positions in the lengthwise direction, —the counter further being adapted to during the process to assemble the counter to the canister, be urged onto the canister until the length of the counter and canister together is within a predefined tolerance of a predefined length.

33 Claims, 4 Drawing Sheets

(56) References Cited

U.S. PATENT DOCUMENTS

| | | |
|---|---|---|
| 2002/0153005 A1 | 10/2002 | Scarrott et al. |
| 2002/0189611 A1 | 12/2002 | Greenwood et al. |
| 2003/0188741 A1 | 10/2003 | Scarrott et al. |
| 2004/0211420 A1 | 10/2004 | Minshull et al. |
| 2004/0255935 A1 | 12/2004 | Bruna |
| 2006/0018991 A1 | 1/2006 | Hoogland |
| 2008/0060643 A1 | 3/2008 | Hodson et al. |

FOREIGN PATENT DOCUMENTS

| | | |
|---|---|---|
| EP | 1369139 | 12/2003 |
| GB | 2288259 | 10/1995 |
| JP | 10-267700 A | 10/1998 |
| WO | WO 86/02275 | 4/1986 |
| WO | WO 96/03172 | 2/1996 |
| WO | WO 96/16686 | 6/1996 |
| WO | WO 98/56444 | 12/1998 |
| WO | WO 01/28887 | 4/2001 |
| WO | WO 01/37909 | 5/2001 |
| WO | WO 02/067844 | 9/2002 |
| WO | WO 2004/001664 | 12/2003 |
| WO | WO 2004/089451 | 10/2004 |
| WO | WO 2006/004497 | 1/2006 |
| WO | WO 2006/004498 | 1/2006 |

* cited by examiner

INHALATION DEVICE AND A METHOD FOR ASSEMBLING SAID INHALATION DEVICE

CROSS-REFERENCE TO RELATED APPLICATIONS

This application is a national phase application under 35 U.S.C. §371 of PCT International Application No. PCT/SE2005/000994, filed Jun. 23, 2005, which claims priority to Swedish Application Serial No. 0401773-7, filed Jul. 2, 2004.

TECHNICAL FIELD OF THE INVENTION

The present invention relates to an inhalation device for delivery of a medicament by inhalation according to the preamble of claim 1. It further relates to a canister and a counter assembly according to the preamble of claim 15 adapted to be positioned in an inhalation device and to a method for assembling said canister and said counter according to the preamble of claim 8.

BACKGROUND OF THE INVENTION AND RELATED ART

Inhalers are commonly used for delivery of a wide range of medicaments. The inhaler holds a canister of medicament, the canister being actuated by compression to deliver a dose of medicament through a mouthpiece to a user.

Canisters for holding a suspension or solution of a pharmaceutical substance in a propellant under pressure are well known. One such known canister to be used in an inhalation device comprises a can coupled with a valve. The valve consists of a body comprising a chamber, a valve stem (which extends from a head of the body) and a metering chamber, selectively communicable by the valve stem to the atmosphere via an L-shaped conduit within the valve body. The valve stem is axially displaceable between a first, extended position in which the metering chamber, and hence the canister, is closed to the atmosphere (since the L-shaped conduit is disposed wholly outside the metering chamber), and a second, depressed position, in which the metering chamber is in open communication with the outlet provided by the L-shaped conduit in the valve stem and through which a metered dose of propellant containing pharmaceutical substance is delivered. The valve stem is inserted into a stem body component, which is part of the mouthpiece and housing of the device. The patient applies a compressive force between the base of the canister, held in an inverted position in the housing, and the stem body which forces the valve stem into the canister. When the valve stem has been depressed sufficiently to open the metering channel, the inhaler will discharge a single dose. This is known as the firing point. This technology is well known and described in many parts of the prior art. For example in Respiratory Drug delivery, Ed Peter Byron, CRC press, 1991, and in Lung Biology in Health and Disease, Vol 94, Inhalation Aerosols, A J Hickey, Publisher Marcel Decker, 1996 and in Pharmaceutical Preformulation and Formulation, Ed Mark Gibson, Chapter 10, Inhalation Dosage Forms, IHS Health Group, 2001.

It is important for the patient to be able to ascertain the level of medicament remaining in the canister. This requirement is met by the use of a dose counter accessory either attached to or part of the inhaler device. It is obvious that this counter must be accurate in that over-counting results in medicament being left in the inhaler unnecessarily resulting in more repeat prescribing with their resultant costs and inconvenience to patient. It also means that in an emergency situation the patient may not use the inhaler in the belief that it is empty when it is not. Conversely, undercounting could result in the inhaler being empty of medicament before the patient has a replacement, which could be dangerous for the patient and reduce patient compliance. Regulatory guidelines require the over and undercounting errors to be minimised.

An inhaler traditionally contains from 120 to 200 doses (shots) so any counter must be reliable, accurate and easy to read. There are many examples of dose counters in the prior art, some located near the valve region of the canister and some attached to the base of the canister which due to the fact that the canister is in an inverted position in the inhaler mouthpiece means that the counter is on the top of the assembled inhaler and can be easily viewed.

In U.S. Pat. No. 6,446,627 a dose counter attached to the base of the actuator is described. The counter measures the displacement of the top of the canister relative to the valve stem. The counter is not attached to the canister and therefore a problem is that the user can swap canisters between actuators and that would cause the indicator of the counter to display the incorrect number of doses remaining in the canister. Furthermore a problem with the inhalation device according to U.S. Pat. No. 6,446,627 is that the actuator and counter assembly are difficult to clean and are vulnerable to damage with water and cleaning products.

In U.S. Pat. No. 4,817,822 a counter attached to the base of the canister, i.e. on the top of the inhalation device, is disclosed. One embodiment of this inhalation device measures the displacement of the canister base relative to the actuator body. A problem with the counter disclosed in U.S. Pat. No. 4,817,822 is miscounting since the counter relies on the displacement of the canister and the canister length due to manufacturing variables is a length with a variable tolerance. A large tolerance of the canister length has the potential to cause miscounting.

In U.S. Pat. No. 6,082,358 a counter attached to the base of the canister is disclosed where the counter counts when a certain force is reached. The counter is attached to the canister but does not require alignment with the actuator body since it relies on the force of the spring in the counter mechanism being less than the force of the spring in the metering valve, such that the counting occurs before firing. A problem with such a counter is that the force of the counting spring and the metering valve need to be accurately controlled, and may vary with use.

However positioning the counter on the base of the canister would be preferred since the visibility of the counter would be good and furthermore the counter could be securely fixed to the canister.

In this text we will refer to a fire point, which is the amount of compression of the canister that is necessary for delivering a dose of medicament and a count point, which is the amount of compression of the canister that is necessary for affecting the counter to count one dose.

SUMMARY

An object of the invention is to provide an inhalation device with a dose counter counting the delivered doses of medicament in a secure and reliable way.

A further object of the invention is to provide an inhalation device where a counter is securely fixed to the canister.

This is achieved in an inhalation device according to claim 1 and in a canister and counter assembly according to claim 15. It is further achieved by a method for assembling the counter and the canister according to claim 8.

Hereby the counter is securely fixed to the canister and the length tolerance of the canister and counter is limited by the controlled fixing of the counter to the base of the canister. Hereby it is possible to provide the counter on the base of the canister (i.e. the top of the inhalation device) and keep the count point close to the fire point and avoid miscounting.

DETAILED DESCRIPTION OF EMBODIMENTS

Figure 1:
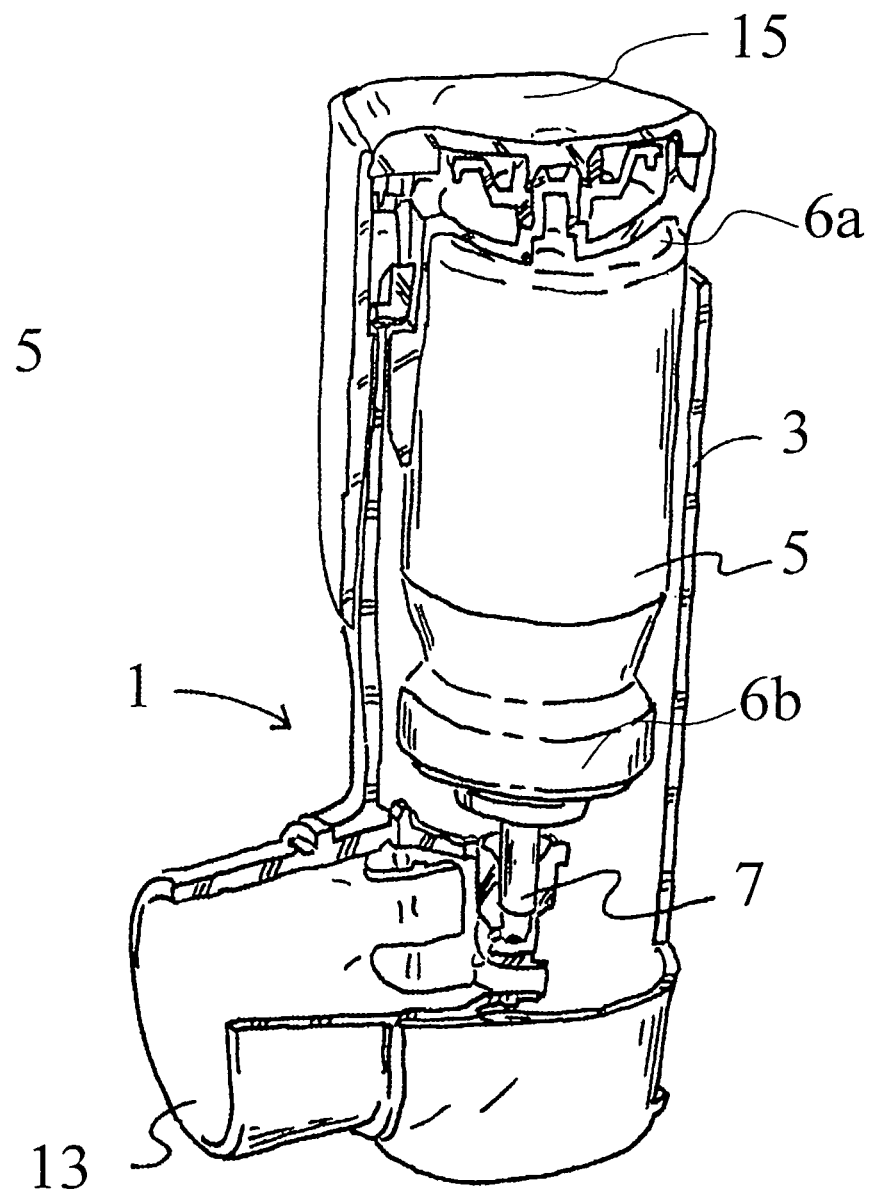
FIG. 1 shows one embodiment of an inhalation device according to the invention.

In FIG. 1 an inhalation device 1 according to one embodiment of the invention is shown. It comprises a housing 3, which encloses a canister 5 holding the medicament. The canister comprises a base end 6a and a valve end 6b. The medicament is delivered to the user through a valve stem 7 connected to the valve end 6b of the canister (lower part of the canister in the figure due to the invert position of the canister in the inhalation device). The medicament is inhaled by the user through a mouth piece 13 that is a part of the housing 3. The mouthpiece is in connection with the valve stem 7 for receiving the medicament to be delivered. Furthermore a dose counter 15 is provided on the base end 6a of the canister, i.e. in the opposite end to the valve stem 7. When a dose of medicament should be delivered to the user the canister 5 is pressed downwards whereby the valve stem is forced into a position where it delivers a dose of medicament. This is in conformity with many inhalation devices according prior art will not be described in more detail here. The dose counter 15 is attached to the canister and will be pressed down together with the canister. The counting is related to the downward motion of the canister and counter. See more detailed description below. The dose counter 15 should increase the number of counted doses by one every time a dose has been delivered. Since undercounting is not to recommend due to the risk that the user believes that there is medicament left in the canister when it actually is empty, the counter usually is affected to count one count only when the canister has been pressed down a distance less than is needed for delivering the dose of medicament. Hereafter the position to where the canister is needed to be pressed down for affecting the counter to count one dose is called the count point and the position to where the canister is needed to be pressed down to deliver one dose is called fire point.

According to the invention the counter is provided onto the base of the canister 5. The counter 15 is attached to the canister 5 in an assembling process and it can be attached to the canister 5 at any one of numerous points along the base part of the canister, i.e. the part of the canister opposite from the valve stem, from the outermost edge of the counter to its inside base giving ranges of variation of positions and varying lengths of canister tolerances. I.e. the counter can be attached anywhere on the base of the canister. The contact areas between the counter and the canister, i.e. the inside of the counter 18 and/or the outside surfaces of the base of the canister 20 (see FIG. 5a), are provided with means for enhancing the friction and ensuring that the counter is fixedly attached to the counter. Different alternatives for this are described in relation to FIGS. 3, 4 and 5 below. In the assembly process the counter 15 is pressed down onto the canister 5 and at the same time the length of the canister together with the counter is measured. The counter 15 is pressed down until a predefined length of the canister and counter together is achieved and this length should also be within a predefined tolerance interval.

Hereby an inhalation device 1 is achieved having a counter securely fixed to the canister and the canister and counter together having a predefined length within a predefined tolerance interval. This is preferred since this allows the control of the distance the canister needs to be depressed before a dose of medicament is delivered and thus also how much the canister needs to be depressed before the counter counts a dose.

Figure 2A:
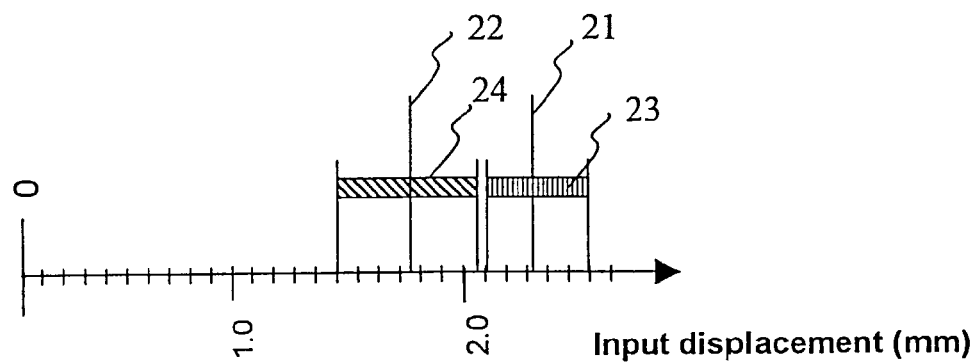
FIG. 2a shows schematically a diagram of the relation between displacement of the canister and the fire and count points in an inhalation device not using the assembly process according to the invention.

FIG. 2a shows schematically how the fire point 21 (dose delivering) and the count point 22 are related to the compression of the canister in an inhaler device where the counter is attached to the base of the canister but the method according to the invention for assembling the counter and canister to achieve a small length tolerance is not used. Hereby the length tolerance of the canister and counter is large. This large length tolerance results in a range of possible counting points 24. This is illustrated in FIG. 2a in that the range of possible count points 24 is larger than the range of possible fire points 23. The range of fire points is only dependent on the valve tolerances and not on the canister length tolerance. The given lengths in FIG. 2a and b for input displacement of the canister are only examples. In reality these could vary for different products. To be absolutely sure that the count point 22 is before the fire point 21 to avoid miscounting, the whole tolerances need to be considered when the position of the count point 22 is decided. The result of this is that the count point 22 needs to be positioned relatively far away from the fire point 21 and in reality this means that the dose counter will count one dose when the canister is pressed down much less than is needed for delivering a dose. This in turn results in a tendency for the counter to overcount the doses and there will actually be medicine remaining when the counter says the canister is empty.

Figure 2B:
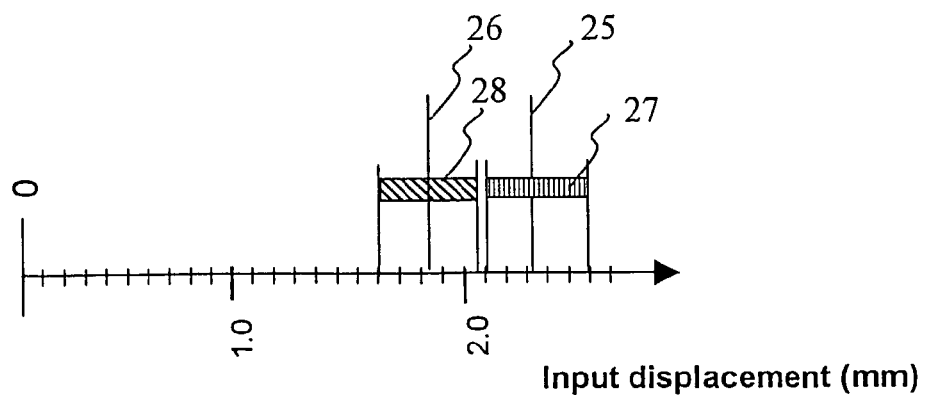
FIG. 2b shows schematically the same as FIG. 2a but for an inhalation device using the assembly process according to the invention.

FIG. 2b shows schematically the same as FIG. 2a but for an inhalation device according to the invention. Here the length tolerance of the canister and counter together is much smaller giving a smaller range of possible count points 28. Therefore the count point 26 can be positioned closer to the fire point 25. Hereby there is less tendency for overcounting.

The counter should be a displacement counter, i.e. a counter that is affected by the displacement of the canister and counts one count each time the canister is pressed down for delivering a dose. As described in the related art chapter there are different examples of such counters available today. One example of a counter that could be positioned onto the base of the canister according to the invention comprises a mechanism to convert longitudinal compression of the canister to a rotational, horizontal movement of an indicating mechanism of the counter. One example of such a counter is described in WO 01/37909. Displacement counters with other kinds of indicating mechanisms are also possible.

To ensure that the counter is fixedly attached to the canister and that the counter can be attached in a range of different positions to the canister one or more of the contact surfaces between the counter and canister (18, 20 FIG. 5*a*) are provided with means for increasing the friction. The means for increasing the friction can be for example roughened areas or deformable means or both. Preferably roughened areas are provided onto the base of the canister. Deformable means can in one embodiment be provided on the inside base of the counter.

Figure 3:
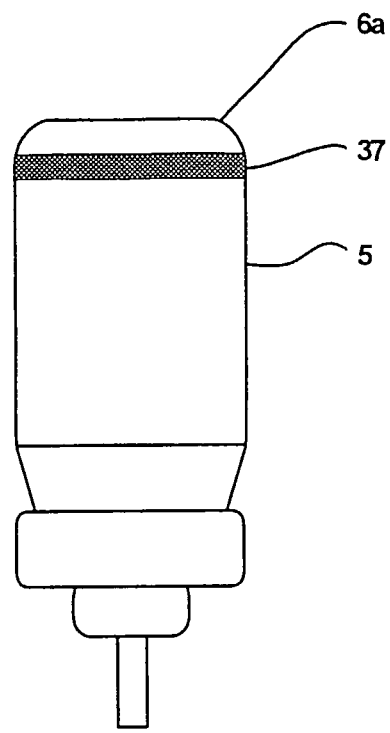
FIG. 3 shows schematically one embodiment of the canister and the positioning of a roughened surface on the canister base.

FIG. 3 shows schematically where roughened areas 37 on the base end 6*a* of the canister 5 can be provided. Preferably the outer side wall at the base of the canister and more preferably the widest part of the wall nearest the base is roughened and the inside of the counter is smooth plastic that deforms into the roughened surface and thereby provides a secure grip. Hereby the counter is securely fixed onto the base of the canister and furthermore the counter may, during the assembly process when the counter is fitted onto the canister, be pressed onto the canister to fit in a range of different positions. The area that should be provided with a roughened surface can vary between different types of canisters but should preferably be provided on the widest part of the base. In another embodiment, the inside of the counter, i.e. the contact surface of the counter (18 in FIG. 5), could also be provided with some kind of roughened surface for increasing the friction. A roughened surface could be produced by for example mechanical working of the surface, knurling the surface, forming grooves into the surface, chemically etching the surface or by laser marked hatching of the surface.

The roughened surface, more precisely, is in one embodiment positioned on the outer wall of the canister at the base end and circumvents the canister, ie it is all the way around the canister side at the widest point of the canister length, see FIG. 3.

The friction between said canister and said counter could also be further increased by means of adhesive. Furthermore the inner surface of the counter could be co-moulded with a high friction coefficient material.

Another possible way of attaching the counter to the base of the canister fixedly to a predefined position is to melt the plastic into a close fit to the canister. An example of this is to use ultra sonic welding or other heating process.

Figure 4:
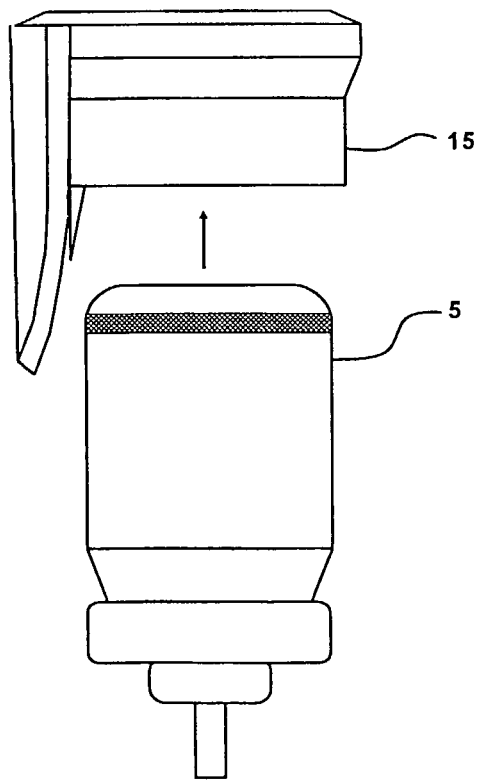
FIG. 4 shows how the counter is attached to the canister.

FIG. 4 shows how the counter 15 is attached to the canister 5.

Figure 5A:
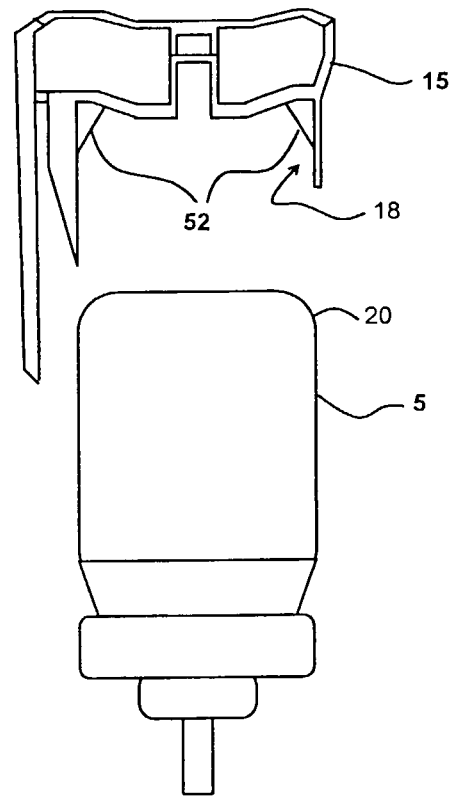
FIG. 5a shows schematically a cross section of one embodiment of the counter and deformable ribs provided on the inside of the counter base before assembly to the canister.

FIG. 5*a* shows schematically a cross section of one embodiment of a counter 15 according to the invention before assembly to the canister 5. In this embodiment deformable means 52 in the form of ribs are provided around the inside of the counter base.

Figure 5B:
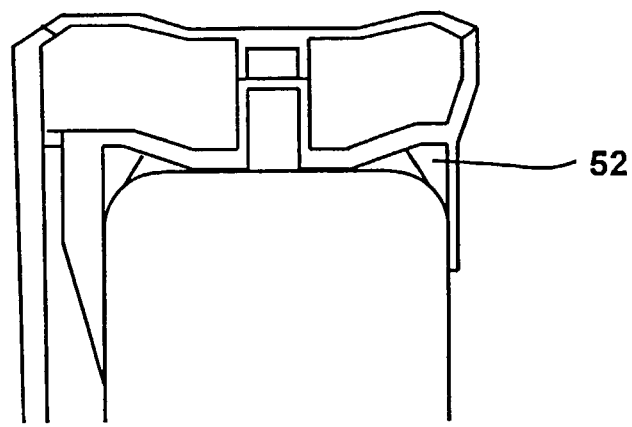
FIG. 5b shows schematically the deformable ribs of FIG. 5a when the counter is assembled to the canister.

FIG. 5*b* shows schematically the deformable ribs of FIG. 5*a* when the counter 15 is assembled to the canister.

The deformable ribs 52 are provided for improving the possibility to control the position of the counter on the base of the canister in a range of different positions. When the counter is pressed onto the base of the canister during the assembly process the deformable ribs are deformed (can be seen in FIG. 5*b*) until the predefined length of the counter and canister together is achieved and then the pressing process is stopped. The force to deform the ribs is higher than the maximum force a patient can apply to the device therefore the canister remains in a fixed position.

The deformable means could be shaped differently and also be positioned in other positions along the inside of the counter than what is shown in FIG. 5. The deformable means could for example be spike shaped features, foam material etc. The deformable means should deform in a controlled manner.

The deformable means could for example be of a rubber material or a polymer material. They could also be co-moulded from two or more materials.

Another method for preventing movement of the counter and canister when assembled is to use a quick setting polymer to deform and fill the space between the counter and canister during the assembly process.

All these different described methods provide a possibility to attach the counter in a range of different positions on the canister and can be used alone or in any combination.

In summary, correct depth alignment of the canister into the counter is achieved by controlling the distance the canister travels into the counter during the assembly process and thereby controlling the overall length tolerances. This is vital to the correct firing and count ratios of the device, encompassing the strict requirements of the regulatory bodies for under and over counting of said counting devices when used in conjunction with a metered dose inhaler system.

The invention claimed is:

1. An inhalation device for delivering doses of medicament to a user comprising:
    a canister having a proximal end and a distal end, said canister having a valve at the distal end and being adapted to accommodate the medicament to be dispensed to a user, one dose of said medicament being dispensed when said canister is pressed down a first predetermined amount, said first predetermined amount being called a fire point; and
    a counter which is connected to the proximal end of the canister and configured to count one dose when said canister is pressed down a second predetermined amount, said second predetermined amount being called a count point,
    wherein at least one of the counter and the canister have a proximally located contact surface for contact between the counter and the canister, the contact surface having a roughened area for increasing the friction between the counter and canister to permit the counter to fixedly be attached onto the canister in a range of different positions in the lengthwise direction such that the combined length of the canister and the counter is variable to within a predefined tolerance.

2. An inhalation device according to claim 1, wherein a portion of the proximal end of the canister includes the roughened area.

3. An inhalation device according to claim 1, wherein the counter includes the contact surface and the roughened area is on an inside surface of the counter having a material different to another material of the counter, wherein the material increases the friction between the counter and the canister.

4. An inhalation device according to claim 1, wherein the counter further includes a deformable material that permits positioning of the counter along the canister in a range of different lengthwise positions within the predefined tolerance.

5. An inhalation device according to claim 4, wherein the deformable material is selected from the group consisting of a polymer rib, a co-molded deformable polymer material, and a quick setting polymer.

6. A method for assembling a canister and a counter in an inhalation device, said canister having a proximal end, a distal end, a valve located at the distal end, and being adapted to accommodate a medicament to be dispensed to a user, one dose of said medicament being dispensed when said canister is pressed down a first predetermined amount, said first predetermined amount being called a fire point, and said counter being connected to the proximal end of the canister and configured to count one dose when said canister is pressed down a second predetermined amount, said second predetermined amount being called a count point, wherein said method comprises:

placing the counter over the proximal end of the canister, at least one of the counter and the canister having a contact surface for contact between the counter and the canister for increasing the friction between the counter and the canister to permit the counter to fixedly be attached onto the canister in a range of different positions in the lengthwise direction;

pushing the counter onto the proximal end of the canister to vary a combined length of the canister and the counter; and measuring the combined length of the canister and the counter until the measured combined length is within a predefined tolerance.

7. A method according to claim 6, wherein the method provides the count point as close before the fire point of the inhaler as the predefined tolerance allows to ensure that the count point does not occur after the fire point.

8. A method according to claim 6, wherein a portion of the proximal end of the canister is formed with the contact surface having a roughened area.

9. A method according to claim 8, wherein the roughened area is formed by at least one of mechanical working, forming grooves in the contact surface, forming laser marked hatchings in the contact surface, and chemical etching.

10. A method according to claim 6, wherein the method comprises forming the counter by co-molding different materials such that an inside surface of the counter comprises a material different to another material of the counter, wherein the material increases the friction between the counter and the canister.

11. A method according to claim 6, wherein the counter is formed in-part with a deformable material and the method further includes positioning of the counter along the canister in a range of different lengthwise positions to at least partially deform the deformable material.

12. A method according to claim 11, wherein said deformable material is selected from the group consisting of a polymer rib, a co-molded deformable polymer, and a quick setting polymer.

13. An inhalation device according to claim 2, wherein the contact surface of the counter includes a smooth plastic material that deforms into the roughened area of the canister to provide a secure grip.

14. An inhalation device according to claim 2, wherein the roughened area of the canister is positioned on an outer wall of the canister that is substantially parallel to a longitudinal axis of the canister and circumvents the canister.

15. An inhalation device for delivering doses of medicament to a user comprising:

a canister having a proximal end and a distal end, said canister having a valve at the distal end and being adapted to accommodate the medicament to be dispensed to a user, one dose of said medicament being dispensed when said canister is pressed down a first predetermined amount, said first predetermined amount being called a fire point; and a counter which is connected to the canister and configured to count one dose when said canister is pressed down a second predetermined amount, said second predetermined amount being called a count point, wherein the proximal end of the canister is adapted to receive the counter, and an inside part of the counter comprises a deformable material that permits lengthwise positioning of the counter onto the canister in a range of different positions such that the combined length of the canister and the counter is variable to within a predefined tolerance.

16. An inhalation device according to claim 15, wherein the deformable material is selected from the group consisting of a polymer rib, a co-molded deformable polymer material, and a quick setting polymer.

17. An inhalation device according to claim 15, wherein the deformable material comprises at least one of a spike shaped feature and a foam material.

18. An inhalation device for delivering doses of medicament to a user comprising:

a canister having a proximal end and a distal end, said canister having a valve at the distal end and being adapted to accommodate the medicament to be dispensed to a user, one dose of said medicament being dispensed when said canister is pressed down a first predetermined amount, said first predetermined amount being called a fire point; and a counter which is connected to the canister and configured to count one dose when said canister is pressed down a second predetermined amount, said second predetermined amount being called a count point, wherein the canister is adapted to receive the counter on the proximal end, such that:

the counter is mounted on the canister at the proximal end thereof, whereby a combined length of the canister and the counter is variable to within a predefined tolerance, the counter includes a plastic material, and the plastic material of the counter is melted into a close fit to the canister.

19. An inhalation device according to claim 18, wherein the plastic material of the counter is melted by ultrasonic heat welding.

20. The inhalation device according to claim 1, wherein the counter is located proximal to the proximal end of the canister.

21. The inhalation device according to claim 1, wherein the counter has an inside surface that includes a first roughened area and the canister has an outer surface that includes a second roughened area that at least partially engages the first roughened area.

22. The inhalation device according to claim 1, wherein the predefined tolerance is less than about 0.5 mm.

23. The inhalation device according to claim 1, wherein the predefined tolerance is about equal to a range of the fire points.

24. The method according to claim 6, wherein the counter is located proximal to the proximal end of the canister.

25. The method according to claim 6, wherein the counter is formed with an inside surface that includes a first roughened area and the canister is formed with an outer surface that includes a second roughened area that at least partially engages the first roughened area.

26. The method according to claim 6, wherein the predefined tolerance is less than about 0.5 mm.

27. The method according to claim 6, wherein the predefined tolerance is about equal to a range of the fire points.

28. The inhalation device according to claim 15, wherein the counter is located proximal to the proximal end of the canister.

29. The inhalation device according to claim 15, wherein the predefined tolerance is less than about 0.5 mm.

30. The inhalation device according to claim 15, wherein the predefined tolerance is about equal to a range of the fire points.

31. The inhalation device according to claim 18, wherein the counter is located proximal to the proximal end of the canister.

32. The inhalation device according to claim 18, wherein the predefined tolerance is less than about 0.5 mm.

33. The inhalation device according to claim 18, wherein the predefined tolerance is about equal to a range of the fire points.

* * * * *